United States Patent [19]
Fenton et al.

[11] Patent Number: 4,911,923
[45] Date of Patent: Mar. 27, 1990

[54] BIOCIDE FOR PETROLEUM OPERATIONS

[75] Inventors: Jeff T. Fenton; John F. Miller, both of Ponca City, Okla.

[73] Assignee: Conoco Inc., Ponca City, Okla.

[21] Appl. No.: 749,246

[22] Filed: Jun. 27, 1985

[51] Int. Cl.$^4$ ............... A61K 31/765; A61K 31/775; C07C 47/10
[52] U.S. Cl. ....................................... 424/82; 568/602
[58] Field of Search ........................... 424/82; 568/602

[56] References Cited
U.S. PATENT DOCUMENTS 2,369,504  2/1945  Walker ................................ 568/602
3,612,178  10/1971  Germer et al. ...................... 166/267

OTHER PUBLICATIONS

Chemical Abstract, vol. 45, (1951) #9910f; Iliceto.

Primary Examiner—Joseph A. Lipovsky
Attorney, Agent, or Firm—C. R. Schupbach

[57] ABSTRACT

An in-situ biocide having improved characteristics comprises polyoxymethylene polymers having an inherent viscosity of at least 0.1 as measured in parachlorophenol at 60° C. Such polymers provide continuous release of formaldehyde biocide in hydrocarbon production, transportation, and storage systems by long term decomposition of the polyoxymethylene. The polyoxymethylenes used are water-insoluble materials, wherein decomposition rate can be controlled through the use of pH, temperature, and certain decomposition catalysts.

4 Claims, No Drawings

BIOCIDE FOR PETROLEUM OPERATIONS

This invention relates to improvements in biocidal treatments in hydrocarbon products and storage systems. More particularly, the present invention provides an improved method for providing a constant effective level of formaldehyde as a biocidal agent, which level can be controlled through the use of temperature, pH and decomposition catalysts. In the oil industry, uncontrolled microbial growth and activity can create severe operational, environmental, and human safety problems. Problems caused or intensified by microbial growth and activity non-exhaustively include corrosion, solids product, oil emulsification, and hydrogen sulfide ($H_2S$) generation.

The microorganisms primarily responsible for corrosion in the oil industry are sulfate reducing bacteria (SRB). These organisms are ubiquitous and can grow in almost any environment. They are routinely found in oil production systems. Even high temperature, salinity and pressure conditions associated with deep oil and gas wells do not prevent their growth and corrosion causing activities (Zobell, Producers Mon. Penn. Oil Production Assoc., 22(7); 12–29, 1958).

The ability of SRB to corrode iron and steel was confirmed over 40 years ago (Bunker, J. Soc. Chem. Ind. 58, 93–100, 1939). Over the years an extensive body of literature has been generated on SRB and other corrosion-causing bacteria. Aspects of microbial corrosion covered in the literature include fundamental corrosion mechanisms, case studies, detection methods and control methods.

Corrosion (pitting) caused by SRB usually results in disproportionate damage. Pipe systems, tank bottoms, and other pieces of oil production equipment can rapidly fail if there are areas where microbial corrosion is occurring. If a failure occurs in a pipeline or oil storage tank bottom, the released oil can have serious environmental consequences. If a failure occurs in a high pressure water or gas line, the consequences may be worker injury or death. Any failure involves repair or replacement costs.

Microorganisms produce solids in several ways. First, microorganisms themselves constitute solids. Secondly, microorganisms growing on the interior surfaces of oil production systems produce a biofilm composed of cells, exopolysaccharide, and adsorbed inorganic debris. Periodically, portions of the biofilm slough off and contribute to the solids loading. SRB produce solids when the sulfide they produce reacts with iron, or other reactive metals, to form insoluble metal sulfides.

Solids create several significant problems for the oil industry. For example, solids in injection waters used during secondary oil recovery operations reduce water injection rates via plugging of the formation into which the water is injected. This results in lower oil production rates and requires costly remedial actions to restore injectivity.

Oil bearing formations typically contain water which is recovered along with the oil during oil production operations. Separating the produced water and oil is a part of oil production operations. Entrained solids can reduce oil/water separation efficiency. Less efficient oil/water separation poses an environmental hazard because of excessive oil concentrations in produced waters treated for environmental discharge. The amount of oil in discharged produced waters can be reduced by biocide treatments to control SRB-generated iron sulfide.

Separating oil and water is more difficult when the oil and water form an emulsion and microorganisms are one cause of emulsification. Microorganisms emulsify oil by producing extracellular products which lower the surface tension between the oil and water. Breaking these emulsions results in increased oil/water separation treatment costs.

$H_2S$ is corrosive and reacts with metal surfaces to form insoluble iron sulfide corrosion products. However, not all of the $H_2S$ produced by SRB is converted to insoluble metal sulfides. Instead the $H_2S$ partitions into the water, oil and natural gas phases of produced fluids and creates a number of problems. For instance, oil and gas which contain high levels of $H_2S$ have a lower commercial value than low sulfide oil and gas. Removing biogenic $H_2S$ from sour oil and gas increases the cost of these products.

$H_2S$ is about as toxic as cyanide gas. It is immediately lethal to man at 1-3 mg/l of air (650-2000 ppm v/v); Kaner, P. *Organic Chemistry*, Elsevier, Amsterdam, 1960), and its presence in the oil field poses a threat to worker safety. Human deaths due to $H_2S$ of biological origin have been reported (Postgate, *Sulfate Reducing Bacteria*, Cambridge University, Cambridge, England, 1979).

The discharge of produced waters containing high levels of $H_2S$ into aquatic or marine environment is hazardous because $H_2S$ reacts with oxygen and lowers the dissolved oxygen levels in water.

Biocide treatments are an effective means for controlling the harmful activity of microorganisms in hydrocarbon production, transportation, and storage systems. However, such systems require long-term protection against microbial activity.

It is well known in the art that formaldehyde is an effective biocide when present in concentrations of at least 50 parts per million, preferably 100 parts per million or more in hydrocarbon production, transportation, and storage systems. Representative but non-exhaustive examples showing formaldehyde-type polymers useful as biocides are U.S. Patents 3,097,129 and 3,293,205 which deal with the use of formaldehyde-yielding short-chain polymers (also known as oligomers) as biocides and insecticides. Other references include U.S. Patent 3,301,752, which teaches disinfecting and sterilizing the compositions in dry form by blending paraformaldehyde together with phenol and iodine in the presence of a binder. U.S. Patent 3,785,971 deals with treatment of waste material wherein from 25 to 75% by weight of the material is paraformaldehyde, a low molecular weight polymer. U.S. Patent 4,125,628 deals with a disinfectant composition comprising quaternary ammonium compounds, phenols, or phenol derivatives and formaldehyde.

In addition, decomposition of oligomers to form a formaldehyde is known, as can be seen from U.S. Patent 885,233. The use of such materials as a disinfectant can be found in U.S. Patent 3,883,303, where a method for controlling odors by inhibiting microorganism growth in septic and holding tanks is set forth, wherein the composition contains borax and paraformaldehyde. U.S. Patent 3,612,178 incidentally mentions the use of formaldehyde as a bacterial inhibiting agent in oil recovery operations.

Thus it is apparent that formaldehyde-bearing low molecular weight polymers or oligomers have found widespread use as bactericides. High molecular weight forms of formaldehyde polymers, known as polyoxymethylene polymers have found widespread use in the plastics industry. Prior to such use, however, these materials are thermally stabilized in order to allow their fabrication. Thermally unstabilized polyoxymethylenes have previously been thought to be useless material with respect to the plastics industry since these materials decompose and do not form useful articles. Aqueous formaldehyde solutions are generated in hydrocarbon production and storage systems by the addition of liquid formalin (37% aqueous formaldehyde) or solid, water soluble paraformaldehyde. Both of these formaldehyde sources are relatively inexpensive and can be cost-effectively used at high concentrations to provide long term biocide protection. However, at high paraformaldehyde treatment concentrations, the risk of worker exposure to hazardous formaldehyde vapors increases. Worker exposure levels to formaldehyde vapors are limited by safety rules. Therefore, a great benefit would result from a safer method whereby cost-effective amounts of formaldehyde could be added to hydrocarbon production, transportation and storage systems for long term biocide protection.

It would therefore be of great benefit to provide a method whereby an effective amount of formaldehyde can be maintained to drilling operations and to other oil related operations such as holding, transportation or storage in order to inhibit bacterial growth, provide a safe means of utilization and which is relatively inexpensive.

It is therefore an object of the present invention to provide an improved method for providing a biocidally effective amount of formaldehyde to hydrocarbon production, transportation, and storage systems. Other objects will become apparent to those skilled in this art as the description proceeds.

We have now discovered an improved method for the use of formaldehyde biocide in hydrocarbon environments, the improvement comprising utilizing as a biocide a water insoluble, polyoxymethylene polymer having an inherent viscosity of at least 0.1 as measured in para-chlorophenol at 60° C. and a minimum melting point of 180° C. to provide a continuous release of formaldehyde upon decomposition of the polyoxymethylene polymer. The undecomposed polymer provides a source of formaldehyde for long term biocide protection, but does not contribute to the release of formaldehyde vapors.

The instant invention can be utilized in drilling fluids to control microbial contamination of oil bearing formations during drilling operations. In packer fluids, the present invention prevents microbial corrosion of casing pipe. When added to a well bore area below the oil bearing zone, use of the present invention helps control microbial activity in an area which is difficult to treat by conventional liquid biocide recirculation treatments. Microbial growth and corrosion in water bottoms of oil storage tanks can also be controlled. Other applications of the invention using formaldehydes as a biocidal agent will be apparent to those skilled in this art.

The terms "hydrocarbon production, transportation and storage" and "hydrocarbon environment" as used herein refer to hydrocarbons containing sufficient water to support and sustain bacterial growth. It will be apparent to those skilled in this art that the presence of bacteria presupposes the presence of water, since bacteria cannot live in a water-free environment.

Normally the amount of formaldehyde can be easily controlled by varying the temperature of the environment. When polyoxymethylene according to the present invention is used at a temperature of from about 20° C. to about 90° C., the environment will be provided with a continuous release of formaldehyde sufficient to maintain a level of at least 50 parts per million in a hydrocarbon environment. Of course it will be realized by those skilled in this art that the amount of polyoxymethylene present, as well as the particle size of such polymer, will have a direct bearing on the amount of formaldehyde released into the hydrocarbon environment. In general, polyoxymethylene is available molded into any given shape, but it is preferred that the fine powder normally obtained from bulk polymerization of trioxane to form polyoxymethylenes, said powder having a molecular weight as determined by inherent viscosity of at least 0.1, be utilized. Lower molecular weight materials (known as paraformaldehydes) normally have the formula $HO(CH_2O)_n$ wherein the n equals from about 8 to about 100. However, when n is greater than about 100, the material becomes water-insoluble and thus becomes very usable as a continuous release low level biocide in hydrocarbon operation.

When the amount of formaldehyde in the hydrocarbon environment is monitored, increases or decreases in the level of formaldehyde present from the decomposing polyoxymethylene can be adjusted by any one or a combination of several methods.

Temperature is one method for controlling the release of formaldehyde from polyoxymethylene. The higher the temperature the more rapid the decomposition of polyoxymethylene and the greater the concentration of formaldehyde in the hydrocarbon environment. Normally such temperatures range from about 20° C. to about 90° C., but temperatures of from about 50° C. to about 80° C. are preferred and temperatures of from 70° C. to 80° C. are more preferred.

A second method for controlling the decomposition of such materials resides in the utilization of pH control. An environment which is strongly acidic or strongly basic enhances the decomposition of such polyoxymethylenes. It has been found that environments which are strongly basic, while enhancing the decomposition of polyoxymethylene, do so at a slower rate than acidic environments. While this is theoretical in nature and we do not wish to be bound thereby, we believe that the basic environment enhances decomposition of polyoxymethylene only from the ends of the polymer chain, whereas an acid environment tends to decompose the polyoxymethylene at several points along the chain, thus effectively decomposing the polyoxymethylene to a paraformaldehyde polymer which becomes water soluble and much more subject to degradation.

A third method of controlling the decomposition of polyoxymethylenes, which can be used alone or in combination with temperature and pH control, is the addition of a decomposition catalyst to the hydrocarbon environment. Such decomposition catalysts are non-exhaustively represented by silica-alumina, alumina, Lewis acids, $BF_3$ and metal halides of the formula $MX_n$ where M is the metal, X is halogen and n is the valence of the metal, such as $AlCl_3$, $BaCl_2$, $ZnCl_2$. These materials, when used in conjunction with pH and temperature control, can effectively regulate the decomposition of polyoxymethylene to provide stable, continuous levels of formaldehyde biocide.

Thus in practice it is preferred that polyoxymethylene be used in a pH environment ranging from about 9.0 to about 12.0, although an acid environment ranging from about 0 to about 3.0 can also be used.

The particle size of the polyoxymethylene polymer utilized in a hydrocarbon environment is not critical other than it be of a size such as to provide adequate formaldehyde levels when subjected to the variables of pH, temperature and catalytic activity. For very long term release, larger particles would be used or a combination of particle sizes such that smaller particles would degrade most quickly to provide formaldehyde while the larger particles would provide a longer term release of formaldehyde. It will be realized by those skilled in the art that the surface area of the polymers is of primary concern in controlling the rate of degradation of polyoxymethylene. Particle size is not critical except that it be such so as to provide the desired level of biocide under the decomposition conditions provided.

Molecular weight of the polyoxymethylene is determined by a combination of inherent viscosity and melting point range (a melting point of at least 180° C., normally from 180° C. to 183° C.). For purposes of longevity, the higher the polyoxymethylene molecular weight, the longer the release life the consequential biocidal activity, especially in high pH environments.

The instant invention is more concretely described with references to the examples, wherein all parts and percentages are by weight unless otherwise specified. The examples are provided to illustrate the present invention and not to limit it.

EXAMPLE 1

Experiments were carried out to show that polyoxymethylene material offers significant advantages over aqueous formaldehyde solutions (37% aqueous formaldehyde) and solid paraformaldehyde as sources of biocidal formaldehyde. All three sources were studies at an active concentration of 1,000 parts per million by weight at temperatures of 30° C., 45° C., and 60° C. In all instances, the concentration of formaldehyde was measured in the vapor phase above solution. Normally concentration was much lower for polyoxymethylene (present as a slurry) than for aqueous formaldehyde or paraformaldehyde (Table I). The inherent viscosity of the polyoxymethylene tested was 0.1 deciliters per gram in parachlorophenol at 60° C.

TABLE 1

| Formaldehyde Vapor Levels (ul/ml) Above Aqueous Solutions Containing 1000 PPMW Active Formaldehyde Source Material | | | |
|---|---|---|---|
| | 30° C. | 45° C. | 60° C. |
| 37% Auqeous Formaldehyde | 6.11 | 6.51 | 27.8 |
| Paraformaldehyde | 0.759 | 6.07 | 26.5 |
| Polyoxymethylene (slurry) | 3.07 | 0.627 | 0.462 |

EXAMPLE 2

Polyoxymethylene was prepared by utilizing 0.1 milliliter of BF$_3$ etherate as a catalyst, 200 grams of purified trioxane in a beaker, melting the trioxane and carrying out a reaction at 75° C. The polymer, when recovered, had an inherent viscosity in parachlorophenol at 60° C. at 1.47 deciliters per gram, and a melting point of 180° C. to 183° C. The polymer was collected, ground, washed with water and acid to purify before using in a test.

The polymer was mixed with water and allowed to stand for 6 days under various conditions of temperature and pH. The formaldehyde concentration of the aqueous solution was determined both for 1,000 and 2,000 milligrams per liter polyoxymethylene concentration in the aqueous slurry. The results after 6 days are set forth in Table 2.

TABLE 2

| Polyoxymethylene Concentration (mg/l) | Formaldehyde Concentration (ppmw) | | | | | | | |
|---|---|---|---|---|---|---|---|---|
| Temperature °C. | 1000 | | | | 2000 | | | |
| pH | 4 | 20 | 35 | 60 | 4 | 20 | 35 | 60 |
| 3 | 0.25 | 0.36 | 1.6 | 94.8 | 0.27 | 0.67 | 3.7 | 95 |
| 7 | 0.25 | 0.25 | 0.6 | 0.8 | 0.50 | 0.38 | 0.51 | 19 |
| 11 | 0.98 | 1.2 | 3.2 | 48.0 | 1.1 | 2.4 | 3.8 | 50 |

EXAMPLE 3

The test described in example 2 was repeated using polyoxymethylene having an inherent viscosity determined as set forth above of .78 deciliters per gram. The tests were repeated using this lower molecular weight polyoxymethylene and the results are set forth in Table 3.

TABLE 3

| Polyoxymethylene Concentration (Mg/l) | Formaldehyde Concentration (ppmw) | | | | | | | |
|---|---|---|---|---|---|---|---|---|
| Temperature °C. | 1000 | | | | 2000 | | | |
| pH | 4 | 20 | 35 | 60 | 4 | 20 | 35 | 60 |
| 3 | 0.22 | 2.2 | 6.0 | 130 | 0.77 | 4.3 | 13.0 | 125 |
| 7 | 0.41 | 2.8 | 3.9 | 90 | 1.5 | 4.8 | 8.5 | 195 |
| 11 | 10.5 | 19.0 | 30.0 | 162.5 | 16.0 | 35.0 | 70.0 | 337 |

EXAMPLE 4

A polyoxymethylene polymer was prepared as described in example 2 to an inherent viscosity determined as described in example 2 of 0.1 deciliters per gram. The polymer so obtained was placed into a solution at a concentration of 1,000 ppmw, the aqueous formaldehyde concentrations were determined at various pH and temperatures after 1 day's incubation. The results are set forth in Table 4.

TABLE 4

| Temperature °C. | Formaldehyde Concentration (ppmw) | | |
|---|---|---|---|
| pH | 20 | 35 | 60 |
| 3 | 2.7 | 18 | 220 |
| 7 | 3.6 | 21 | 240 |
| 11 | 90 | 570 | 410 |

When comparing the data presented in tables 2, 3 and 4, it is apparent that the decomposition of the formaldehyde proper materials as measured by formaldehyde concentration was a function of pH, temperature, polymer concentration and inherent viscosity.

EXAMPLE 5

A 0.1 deciliter per gram polyoxymethylene polymer prepared as described in example 2 was placed into an aqueous media as a slurry at a concentration level of 1,000 parts per million by weight. The sample was divided into 3 portions. Into one sample was placed 1% silica-alumina decomposition catalyst (1 gram to 99 grams) (AGZ-200 FCC, trademark of and sold by Davison Chemical Divisions of WR Grace and Co.), and into the second portion was placed 2% silica alumina decomposition catalyst, levels of silica alumina being based on the total weight of the polymer and 37% silica alumina into the third portion. Each slurry containing various concentrations of silica alumina catalysts was divided into aliquots containing representative quantities of catalysts and polyoxymethylene polymers and subjected to various pH and temperature conditions. Thereafter the formaldehyde concentration in the solution was determined by the test set forth in example 2. Results of these experiments are set forth in Table 5.

TABLE 5

| | Formaldehyde Concentrations, ppmw | | | | | | | | |
|---|---|---|---|---|---|---|---|---|---|
| | % $SiO_2/Al_2O_3$ Temperature (°C.) | | | | | | | | |
| | 1% | | | 2% | | | 3% | | |
| pH | 20 | 35 | 60 | 20 | 35 | 60 | 20 | 35 | 60 |
| 3 | 2.7 | 2.7 | 410 | 3.1 | 4.1 | 570 | 3.8 | 3.8 | 340 |
| 7 | 25.0 | 32.0 | 630 | 190.0 | 26.0 | 380 | 20.0 | 56.0 | 510 |
| 11 | 310.0 | 390.0 | 740 | 280.0 | 400.0 | 790 | 320.0 | 350.0 | 470 |

The results indicate that the presence of the catalyst assisted decomposition of the polymer at high temperature as compared to the Table 4 results.

EXAMPLE 6

Biocidal properties of polyoxymethylene polymer having an inherent viscosity of 0.78 deciliters per gram at a concentration of 1500 parts per million by weight was tested against aerobic bacteria cultures. Aerobic and anerobic heterotropic bacteria were obtained from field cultures made from produced water from Cat Canyon field, Ventura, California, and the Big Muddy Wyoming field. The field cultures were mixed with laboratory strains of *Pseudomonas aeruginosa, P. fluorescens, Bacillus cereus,* and sulfate reducing bacteria (SRB) to ensure that common problem-causing bacteria were present together with bacteria obtained from produced waters.

Viable bacteria were determine over a period of time ranging up to one week. Three different pH levels and 3 temperature ranges within each pH level were tested. The effectiveness of polyoxymethylene in reducing and/or eliminating these aerobic bacteria over a period of time is set forth in Table 6 and 7.

TABLE 6

| | Total Aerobic Bacteria per ml | | | | | | | | | | | | | | | | | |
|---|---|---|---|---|---|---|---|---|---|---|---|---|---|---|---|---|---|---|
| | pH | | | | | | | | | | | | | | | | | |
| | 7 | | | | | | 9 | | | | | | 11 | | | | | |
| | Temp (°C.) | | | | | | | | | | | | | | | | | |
| | 30 | | 40 | | 50 | | 30 | | 40 | | 50 | | 30 | | 40 | | 50 | |
| | Control | Test | Control | Test | Control | Test | Control | Test | Control | Test | Control | Test | Control | Test | Control | Test | Control | Test |
| Time | | | | | | | | | | | | | | | | | | |
| 0 Hour | $10^7$ | $10^7$ | $10^7$ | $10^7$ | $10^7$ | $10^7$ | $10^7$ | $10^7$ | $10^7$ | $10^7$ | $10^7$ | $10^7$ | $10^7$ | $10^7$ | $10^7$ | $10^7$ | $10^7$ | $10^7$ |
| 2 Days | $\geq 10^9$ | $\geq 10^9$ | $10^5$ | $10^9$ | $10^3$ | $10^2$ | $10^6$ | $10^6$ | $10^7$ | $10^4$ | $10^3$ | $10^2$ | $10^3$ | $10^3$ | $10^2$ | $10^1$ | $10^3$ | 0 |
| 7 Days | $\geq 10^9$ | $\geq 10^9$ | $\geq 10^7$ | $\geq 10^7$ | $10^2$ | 0 | $\geq 10^9$ | $10^8$ | $10^6$ | $10^3$ | $10^2$ | 0 | $10^3$ | 0 | 0 | 0 | 0 | 0 |

TABLE 7

| | Sulfate Reducing Bacteria per ml | | | | | | | | | | | | | | | | | |
|---|---|---|---|---|---|---|---|---|---|---|---|---|---|---|---|---|---|---|
| | pH | | | | | | | | | | | | | | | | | |
| | 7 | | | | | | 9 | | | | | | 11 | | | | | |
| | Temp(°C.) | | | | | | | | | | | | | | | | | |
| | 30 | | 40 | | 50 | | 30 | | 40 | | 50 | | 30 | | 40 | | 50 | |
| | Control | Test | Control | Test | Control | Test | Control | Test | Control | Test | Control | Test | Control | Test | Control | Test | Control | Test |
| Time | | | | | | | | | | | | | | | | | | |
| 0 Hour | $10^6$ | $10^6$ | $10^6$ | $10^6$ | $10^6$ | $10^6$ | $10^6$ | $10^6$ | $10^6$ | $10^6$ | $10^6$ | $10^6$ | $10^6$ | $10^6$ | $10^6$ | $10^6$ | $10^6$ | $10^6$ |
| 2 Days | $\geq 10^5$ | $\geq 10^5$ | $\geq 10^5$ | $\geq 10^5$ | $10^4$ | $10^4$ | $\geq 10^5$ | $\geq 10^5$ | $\geq 10^5$ | $10^4$ | $\geq 10^5$ | $\geq 10^5$ | $\geq 10^5$ | $\geq 10^5$ | $10^4$ | $10^2$ | $10^4$ | $10^2$ |
| 7 Days | $\geq 10^5$ | $\geq 10^5$ | $\geq 10^5$ | $\geq 10^5$ | $10^3$ | $10^3$ | $\geq 10^5$ | $\geq 10^5$ | $\geq 10^5$ | $10^4$ | $10^4$ | 0 | $10^4$ | $10^4$ | $10^4$ | $10^1$ | $10^2$ | 0 |

At conditions shown to favor decomposition of polymeric formaldehyde (inherent viscosity of at least 0.1), such as pH at temperatures, the levels of bacteria are significantly reduced by the released formaldehyde.

Thus the present invention provides improved method for providing formaldehyde biocide at predetermined levels utilizing a water insoluble polyoxymethylene polymer having an inherent viscosity as measured in parachlorophenol at 60° C. of at least 0.1 deciliters per gram and a melting point of at least 180° C. The rate of release can be altered by controlling the concentration, pH, temperature or by the addition of a catalyst to enhance decomposition of the polymer to form formaldehyde or paraformaldehyde to provide biocidal activity.

While certain embodiments and details have been shown for the purpose of illustrating this invention, it will be apparent to those skilled in this art that various changes and modifications may be made herein without departing from the spirit or scope of the invention.

We claim:

1. A method for maintaining an effective concentration of formaldehyde biocide in water-containing petroleum hydrocarbon production, transportation and storage systems comprising utilizing as a biocide in said water-containing petroleum hydrocarbon systems a water insoluble polyoxymethylene having a high molecular weight as defined by an inherent viscosity of at least 0.1 as measured in para-chlorophenol at 60° C. and having a melting point of at least 180° C. to provide continuous release of formaldehyde sufficient to maintain a constant, substantially vapor free concentration of formaldehyde of at least 50 parts per million in said water-containing petroleum hydrocarbon systems upon controlled decomposition of said polyoxymethylene.

2. A method as described in claim 1 wherein the polyoxymethylene is decomposed in a water containing hydrocarbon environment at a temperature of from about 35° C. to about 90° C.

3. A method as described in claim 2 wherein the polyoxymethylene is used in a pH environment ranging from about 9.0 to about 12.0.

4. A method is described in claim 3 wherein the polyoxymethylene contains a decomposition catalyst in an amount sufficient to degrade the polyoxymethylene at a controlled rate to maintain a substantially constant level of formaldehyde, wherein the decomposition catalyst is selected from the group consisting of silica alumina, alumina, Lewis acids, $BF_3$ and metal halides of the formula $MX_n$, where M is a metal, X is halogen and n is the valence of metal M.

* * * * *